United States Patent [19]
Chowdhary

[11] Patent Number: 5,104,410
[45] Date of Patent: Apr. 14, 1992

[54] SURGICAL IMPLANT HAVING MULTIPLE LAYERS OF SINTERED POROUS COATING AND METHOD

[75] Inventor: Prataprai R. Chowdhary, Round Rock, Tex.

[73] Assignee: Intermedics Orthopedics, Inc, Austin, Tex.

[21] Appl. No.: 600,945

[22] Filed: Oct. 22, 1990

[51] Int. Cl.$^5$ ............................................... A61F 2/26
[52] U.S. Cl. ......................................... 623/11; 427/2; 427/405
[58] Field of Search ...................... 427/2, 405; 623/11, 623/16, 20, 22

[56] References Cited

U.S. PATENT DOCUMENTS

| | | | |
|---|---|---|---|
| 4,702,930 | 10/1987 | Heide et al. | 623/16 |
| 4,813,965 | 3/1989 | Roberts | 623/16 |
| 4,854,496 | 8/1989 | Bugle | 623/22 |
| 4,902,535 | 2/1990 | Garg et al. | 427/405 |

*Primary Examiner*—Randall L. Green
*Assistant Examiner*—Gina M. Gualtieri
*Attorney, Agent, or Firm*—John R. Merkling

[57] ABSTRACT

A surgical prosthetic device for implant in a patient and method for making said device, the device comprising a composite structure having a solid metal substrate and a porous coating with multiple sintered layers. The porous coating has an external layer to accept bone ingrowth. An intermediate layer bonds the external porous layer to the substrate. The layers are applied in a process of multiple sintering, whereby each successive layer is individually sintered to the substrate or to the proceeding layer, as applicable. This process provides a porous area having increased strength of attachment between the substrate and the external porous layer. An acid etch solution promotes adhesion between the substrate and the intermediate layer thus increasing the consistency of the process. The initial sintering is held at elevated temperature for less time than the sintering of the external layer. At the end of each sintering step, the prosthesis is quick cooled using an inert gas, preferably helium.

20 Claims, No Drawings

SURGICAL IMPLANT HAVING MULTIPLE LAYERS OF SINTERED POROUS COATING AND METHOD

FIELD OF THE INVENTION

My invention relates to surgical prosthetic devices having porous metal coatings on substrate surfaces.

BACKGROUND OF THE INVENTION

In the field of implantable prosthetic devices, it is known that adhesion of a prosthesis to adjacent bone tissue can be promoted by providing a porous layer or area for ingrowth of bone. Bone tends to grow into interstices in the porous area, thereby securing the prosthesis. However, the metallic substrate of the prosthesis and the porous layer have different materials properties, particularly if different substances are used in the substrate and the porous layer. Adhesion between the substrate and the porous layer continues to be a matter of development in this field.

Several techniques have been proposed in the ongoing effort to adhere an appropriate porous layer to a substrate. For example, Hahn proposed in U.S. Pat. No. 3,605,123 that a dense base metal be coated with a porous film of the same material. The porous film was applied by a flame spray process, such as plasma flame processing. In U.S. Pat. No. 3,855,638, Pilliar described a prosthetic device having a solid metallic substrate with a porous coating adhered thereto. The porous coating was described as extending partially over the surface of the substrate. A slurry of metallic particles was applied to the substrate, dried and then sintered. Since both the substrate and the powder were involved in the sintering step, thermal stresses encountered by prior art methods were avoided. On different areas of the substrate, metallic particles of different sizes might be used, depending on whether a particular area of the prosthesis was expected to be adjacent hard or soft tissue.

Bokros, in U.S. Pat. No. 4,038,713, also employed sintering to affix coils in grooves of a prosthesis or to produce porous metallic tubes having some flexibility. Thereafter, in U.S. Pat. No. 4,206,516, Pilliar suggested the use of a thermally decomposable compound for the metallic particles. An example would have been titanium hydride particles. To affix the thermally decomposable compound to the substrate, two heating stages would be proposed, first for thermal decomposition and then for sintering.

In each of the patents mentioned above, the porous coat comprised metallic particles of a single size. In U.S. Pat. No. 4,524,539, Rowe, et al., described the preparation of a porous coating comprising multiple layers with progressively larger particles in subsequent layers. Hahn was a co-inventor of this patent. To deposit these layers on the substrate, a flame plasma process was described, similar to the process previously described by Hahn in his earlier Pat. No. 3,605,123 patent.

SUMMARY OF MY INVENTION

I have invented a surgical prosthetic device for implant in a patient comprising a composite structure having a solid metal substrate and a porous coating with multiple sintered layers. The porous coating has an external layer to accept bone ingrowth. An intermediate layer bonds the external porous layer to the substrate. The layers are applied in a process of multiple sintering, whereby each successive layer is individually sintered to the substrate or to the proceeding layer, as applicable. This process provides a porous area having increased strength of attachment between the substrate and the external porous layer.

To prepare the substrate, I have provided an acid etch solution to promote adhesion between the substrate and the intermediate layer thus increasing the consistency of the process.

I have also found that such multiple sintering should take place under particular conditions of vacuum and temperature, with the initial sintering being held at elevated temperature for less time than the sintering of the external layer. At the end of each sintering step, the prosthesis should be quick cooled using an inert gas, preferably helium.

DETAILED DESCRIPTION OF MY PREFERRED EMBODIMENT

My preferred embodiment of a surgical prosthetic device according to my present invention comprises a metallic substrate, preferably of a cobalt chrome alloy. Cobalt chrome alloy appears to exhibit superior wear characteristics with adjacent polyethylene bearing surfaces in prosthetic devices such as artificial knees or hips. A porous layer is applied to a surface of the prosthesis, either on an exterior surface, or in a recessed area. I prefer to use titanium for the metal of the porous layer. Titanium provides a superior bone interface, so that bony ingrowth into the porous layer can be promoted. The porous coating itself is attached to the cobalt chrome substrate through an intermediate layer of titanium which provides a transition between the substrate and the porous layer.

I will now describe my preferred method for applying a titanium porous layer to a cobalt chrome substrate. I prefer to use ASTM F 75 OR ASTM F 799 cobalt chrome for a substrate. An area on the substrate to be coated should be prepared by vapor decreasing in freon for between three to five minutes. The substrate area should then be etched with an acid etch solution for three minutes. In my preferred embodiment, the acid etch solution comprises a mixture by volume of 30 milliliters of 40% hydrofluoric acid, 470 milliliters of 70% nitric acid, and 500 milliliters deionized water. This acid etch solution, and all other solutions described herein, should be prepared before processing starts and the solutions should be available for prompt application during processing. In tests, the acid etch improved the consistency of the subsequent process, so that the porous layer was more uniformly bonded to the substrate.

After etching, I rinse the substrate, preferably twice, in tap water. I then dry the substrate by dipping it in an alcohol bath. The alcohol bath is preferably 190 proof ethyl alcohol. The substrate is then blown dry under a warm air blower. The surface is prepared by grit blasting using 60 grit alumina, under a pressure of 60 psi. A second grit blast is then performed using 20 grit alumina, under a pressure of 100 psi. After grit blasting, the substrate is cleaned in an ultrasonic bath at room temperature. The bath comprises an alconox solution of 4 grams of alconox detergent power combined with one liter of tap water.

After ultrasonic cleaning, the substrate should be again rinsed with tap water, and dried in the alcohol bath. The substrate should then be blown dry under a warm air dryer for 10 to 20 minutes.

I then apply the interface layer of titanium. I prepare the titanium interface layer by pouring a few grams of titanium powder graded through 325 mesh into a dish and mixing it into a slurry with a small quantity of alcohol. Using a brush, I paint the titaniux alcohol slurry on the areas of the substrate intended for porous coating. These areas may be recessed into the substrate to form pockets. After the paint is dried, a thin latter of titanium powder remains on the surface. The prosthetic device is then ready to be sintered for the first time.

I place the device in a vacuum furnace with a vacuum of between $10^{-5}$ and $10^{-6}$ torr. The furnace temperature is then elevated to 1100° C., and that temperature is maintained one hour. The substrate and intermediate layer are then quick cooled using helium gas until the substrate reaches a temperature of about 35° C. In my preferred embodiment, I use a tank of helium gas which is at room temperature. It is expected that the helium gas will be cooled by the venturi effect on escaping from the tank. The stream of gas is passed over the heat exchanger of the vacuum furnace and then onto the prosthetic substrate. The approximate rate of cooling is about 50° to 100° C./min. After the device has cooled, it is removed from the furnace.

I then apply the porous titanium layer. I first prepare the prosthetic device for the porous layer by grit blasting the pocket areas with 20 grit alumina, at 100 psi. The device is then cleaned with the alconox solution in the ultrasonic bath. I then rinse the device, preferably twice, with tap water. After rinsing., the device is dried by dipping it in the alcohol bath and by blow drying the device under a warm air blower between 10 to 20 minutes.

I then place the device in a conformal mold, adapted to be compressed in an hydraulic press. A mixture of commercially pure titanium, called hereafter the porocyl mixture, is applied to the pockets of the prosthetic device. The porocyl mixture comprises commercially pure titanium particles separated through a mesh size of between 100 and 200, together with a urea pore former of a mesh size between 35 and 50. The urea and titanium are mixed in weight proportions of 2940 parts urea to 6860 parts titanium. The mixture is combined in a blender for about 10 minutes and then 98 parts alcohol by weight are added and the mixture is blended for an additional 15 minutes.

After the porocyl mix has been placed in the pockets, it should be pressed in a with a die using a hydraulic press at a load between 300 to 400 tons resulting in a pressure of approximately 20,000 to 30,000 psi. The device should then be green finished to remove excess porocyl mix. I then soak the device in tap water maintained at a temperature between 20° C. and 38° C. for between 1 and 1.5 hours.

The device is then rinsed with tap water from 5 to 15 minutes and ultrasonically cleaned with water for 45 seconds. The device is dried by dipping it in the alcohol bath and blow dried under the warm air blower for between 10 to 20 minutes.

The device is then ready for its second sintering. I place the device in the vacuum furnace under a vacuum of from $10^{-5}$ to $10^{-6}$ torr and heat to 1030° C. That temperature is maintained 2 hours, and the device is then quick cooled with helium through to about 35° C., as described above.

I have observed that several steps in the process described above significantly effect the strength of adhesion between the porous layer and the substrate. The strength of adhesion was tested by attaching a test button to the porous layer with an adhesive and pulling the the substrate and the test layer in tension to failure. Adding the intermediate layer of titanium, without more, increased the strength of adhesion by 16 per cent. By grit blasting the intermediate layer, the strength of adhesion could be increased by 30 per cent. I also compared the effect of using 1030° C. for the second sintering temperature rather than 900° C. I found that using the higher temperature increased the strength of adhesion by 30 per cent. Similarly, maintaining the sintering temperature for a longer period of time (that is, two hours instead of half an hour) increased the strength by 10 percent. It is also important that after cooling the device as described above, there is no tempering or stress relief step. I found that the omission of such a step resulted in a further 10 per cent gain in strength of adhesion. By optimizing the process as I have described above, I was able to increase the strength of adhesion by between 50 and 70 per cent over all.

My invention may be used in other ways without departing from the essential characteristics thereof. The scope of my invention is defined by, the following claims rather than the foregoing description and all variations within the scope of equivalency of the claims are intended to be encompassed therein.

I claim as my invention:

1. A prosthetic implant comprising the combination of a metallic substrate and a porous metallic layer on at least a portion of said substrate, said porous metallic layer being of different composition from said metallic substrate, the porous layer being joined to said substrate through an intermediate, non- porous layer, said intermediate layer having substantially the same composition as the porous layer.

2. A prosthetic implant according to claim 1 wherein the substrate is comprised of cobaslt chrome alloy and wherein the porous layer and the intermediate layer are comprised of titanium.

3. A method of applying a porous coating to a selected portion of surface of a prosthetic implant substrate comprised of a first metallic substance, the method comprising the successive steps of:
    cleaning at leas the selected portion of the surface of the substrate;
    applying a slurry containing a powder comprised of a second metallic substance to said selected portion;
    drying said slurry to leave at least said powder as a residue on said selected portion;
    sintering said powder on said substrate to form an intermediate metallic layer;
    applying a mixture comprised of a particulate and a filler material for forming pores, said particulate being comprised substantially of said second metallic substance, and
    sintering said mixture on said intermediate layer.

4. The method according to claim 3 wherein the step of sintering said powder further comprises
    placing said substrate in a sintering furnace;
    evacuating air from said furnace;
    elevating temperature in said furnace;
    maintaining said temperature for a first predetermined length of time; and
    cooling said substrate; and wherein the step of sintering said mixture further comprises
    re-placing said substrate in a sintering furnace;
    re-evacuating air from said furnace;
    re-elevating temperature in said furnace;

maintaining said temperature for a second predetermined length of time, said second period of time being longer than said first period of time; and re-cooling said substrate.

5. The method according to claim 4 wherein the step of evacuating air from said furnace comprises creating a vacuum of from $10^{-5}$ to $10^{-6}$ torr, and wherein the step of elevating temperature in said furnace comprises elevating the temperature to about 1100° C., and wherein said first length of time is about one hour.

6. The method according to claim 5 wherein the step of cooling said substrate comprises passing a stream of an inert gas over said substrate.

7. The method according to claim 6 wherein the step of cooling the substrate comprises cooling the substrate at a rate of about 50 to 100° C./min. to about 35° C.

8. The method according to claim 3 wherein the step of re-evacuating air from said furnace comprises creating a vacuum of from $10^{-5}$ to $10^{-6}$ torr, and wherein the step of re-elevating the temperature in said furnace comprises elevating the temperature to about 1030° C., and wherein said second length of time is about two hours.

9. The method according to claim 8 wherein the step of cooling said substrate comprises passing a stream of an inert gas over said substrate.

10. The method according to claim 9 wherein the step of cooling the substrate comprises cooling the substrate at a rate of about 50° to 100° C./min. to about 35° C.

11. The method according to claim 3 wherein the substrate comprises a cobalt-chrome alloy, and wherein the metallic powder and the metallic particulate comprise titanium.

12. The method according to claim 3 wherein the step of cleaning the selected portion of the surface comprises etching the portion of the surface with acid; and grit blasting the portion of the surface.

13. The method according to claim 12 wherein the step of applying said metallic particulate further comprises grit blasting the portion of the surface; and pressing the metallic particulate onto said portion of the surface with a pressure between 30,00 and 40,000 psi.

14. The method according to claim 13 wherein the step of sintering said metallic powder further comprises placing said substrate in a sintering furnace;

evacuating air from said furnace;

elevating temperature in said furnace;

maintaining said temperature for a first predetermined length of time; and cooling said substrate; and wherein the step of sintering said mixture further comprises re-placing said substrate in a sintering furnace;

re-evacuating air from said furnace;

re-elevating temperature in said furnace; predetermined length of time; said second period of time being longer than said first period of time; and re-cooling said substrate.

15. The method according to claim 14 wherein the step of evacuating air from said furnace comprises creating a vacuum of from $10^{-5}$ to $10^{-6}$ torr, and wherein the step of elevating temperature in said furnace comprises elevating the temperature to about 1100° C., and wherein said first length of time is about one hour.

16. The method according to claim 15 wherein the step of cooling said substrate comprises passing a stream of an inert gas over said substrate.

17. The method according to claim 14 wherein the step of cooling the substrate comprises cooling the substrate at a rate of about 50° to 100° C./min. to about 35° C.

18. The method according to claim 15 wherein the step of re-evacuating air from said furnace comprises creating a vacuum of from $10^{-5}$ to $10^{-6}$ torr, and wherein the step of re-elevating the temperature in said furnace comprises elevating the temperature to about 1030° C., and wherein said second length of time is about two hours.

19. The method according to claim 16 wherein the step of cooling said substrate comprises passing a stream of an inert gas over said substrate.

20. The method according to claim 19 wherein the step of cooling the substrate comprises cooling the substrate at a rate of about 50° to 100° C./min. to about 35° C.

* * * * *